United States Patent
Beshay

(10) Patent No.: US 12,066,419 B1
(45) Date of Patent: *Aug. 20, 2024

(54) SENSOR AND METHOD FOR RAPID IN SITU DETECTION OF TOXIC GASES

(71) Applicant: Intelligent Optical Systems, Inc., Torrance, CA (US)

(72) Inventor: Manal Beshay, Rancho Palos Verdes, CA (US)

(73) Assignee: Intelligent Optical Systems, Inc., Torrence, CA (US)

( * ) Notice: Subject to any disclaimer, the term of this patent is extended or adjusted under 35 U.S.C. 154(b) by 937 days.

This patent is subject to a terminal disclaimer.

(21) Appl. No.: 16/531,613

(22) Filed: Aug. 5, 2019

Related U.S. Application Data

(60) Continuation of application No. 14/089,627, filed on Nov. 25, 2013, now Pat. No. 10,401,343, which is a division of application No. 12/892,566, filed on Sep. 28, 2010, now abandoned.

(51) Int. Cl.
*G01N 33/00* (2006.01)

(52) U.S. Cl.
CPC ..... *G01N 33/0057* (2013.01); *G01N 33/0052* (2013.01)

(58) Field of Classification Search
CPC ........... G01N 33/0057; G01N 33/0052; G01N 33/22; G01N 33/00; G01N 21/72; G01N 21/62; G01N 21/00
USPC ........................................... 422/86; 436/124
See application file for complete search history.

(56) References Cited

U.S. PATENT DOCUMENTS

| | | | |
|---|---|---|---|
| 4,399,099 A | 8/1983 | Buckles | |
| 4,834,496 A | 5/1989 | Blyler | |
| 4,846,548 A | 7/1989 | Klainer | |
| 5,138,153 A | 8/1992 | Gergely | |
| 5,378,432 A | 1/1995 | Bankert | |
| 6,420,181 B1 * | 7/2002 | Novak | G01N 31/22 210/658 |
| 6,535,658 B1 | 3/2003 | Mendoza | |
| 7,260,283 B2 | 8/2007 | Lieberman | |
| 7,551,810 B2 | 6/2009 | Berger | |
| 7,583,865 B2 | 9/2009 | Berger | |
| 7,650,051 B2 | 1/2010 | Lieberman | |
| 7,671,325 B2 | 3/2010 | Sanders | |
| 7,702,189 B2 | 4/2010 | Sanders | |
| 2007/0087444 A1 * | 4/2007 | England | G01N 31/224 436/166 |

OTHER PUBLICATIONS

Beshay et al, Recent advances toward a fiber optic sensor for nerve agent, 2008, Proc. of SPIE, 6954, 69540F1-10 (Year: 2008).*

* cited by examiner

*Primary Examiner* — Christine T Mui

(57) ABSTRACT

A sensor and method for the rapid detection of fluoride containing gaseous species specifically the chemical warfare agents Sarin and Soman nerve gas, in which a chemically sensitive composition containing dye indicator molecules complexed with a heavy metal salt is exposed to an environment under surveillance for toxic gasses. In one embodiment the sensing composition is introduced into a polymer-based substrate. The detection composition reacts with hydrogen fluoride which is a decomposition by-product of Sarin and Soman gas so as to change the color of the dye indicator, in one embodiment being pentamethoxy red, that is to change the color of the polymer-based substrate from colorless to a dark purple color. The complex of pentamethoxy red with the exemplary heavy metal salt, zirconyl chloride, is specific for Sarin and Soman nerve gas; it does not react to certain other toxic gases. In various embodiments a hydrolyzing agent is introduced in the polymer-based substrate to improve the detection reaction sensitivity and to increase the reaction rate and decrease the detection time for sensor chemistry.

18 Claims, 15 Drawing Sheets

ABSORBANCE MEASUREMENT @632nm_00
POLY 126 GD 000, AND 10mg/m$^3$
CUBRC T120208 MEAS05-07
TEST GAS INITIATED AT 300 SEC.

TIME (sec.)
FIBER RESPONSE TO 100 AND 10 mg/m$^3$ SOMAN VAPORS

FIG. 11

SENSOR AND METHOD FOR RAPID IN SITU DETECTION OF TOXIC GASES

RELATED APPLICATIONS

This application claims priority to and is a continuation of application Ser. No. 14/089,627 filed on Nov. 25, 2013, now U.S. Pat. No. 10,401,343, and is a divisional application of application Ser. No. 12/892,566 filed on Sep. 28, 2010, now abandoned, both of which are incorporated herein in their entirety.

GOVERNMENT LICENSE RIGHTS

This invention was made with Government support under TSWG contract N41756-03-C-4048. The Government has certain rights in the invention.

TECHNICAL FIELD

The present invention relates to detection of gas. It relates to chemistry for the detection of gas, in particular the detection of fluoride containing gases more specifically the detection of the nerve gases Sarin and Soman by way of their decomposition by-products. It relates to chemo-chromic sensors for the detection of fluoride in the gas phase, in particular the nerve gases, Sarin and Soman. It relates to optical sensors for the detection of gas, in particular distributed intrinsic fiber optic sensors and in general waveguide sensors and systems incorporating the combination of sensing indicator chemistry and optical sensing means.

BACKGROUND

The fluorinated organophosphate nerve agents Tabun (GA), Sarin (GB), Soman (GD), and Cyclosarin (GF) are among the most toxic chemical warfare agents known. Together they comprise the G-series nerve agents, thus named because German scientists first synthesized them, beginning with GA in 1936. GB was discovered next in 1938, followed by GD in 1944 and finally the more obscure GF in 1949.

Sarin gas (O-Isopropyl methylphosphonofluoridate) and Soman gas O-Pinacolyl methylphosphonofluoridate), are colorless and odorless nerve gases, and since they are extremely volatile can spread quickly through the air. Nerve gas attacks may come unexpectedly. It is important to be able to detect them at a high level of sensitivity because a gas cloud tends to disperse into low density portions and strands. It is also desirable to do so in a manner to communicate its detection quickly through an automated system and to enable detection over a distance.

The detection of nerve gases including Sarin and Soman at as early a time in the attack is critical to ameliorating or minimizing the consequences of the attack.

There are several methods for detecting Sarin and Soman which include spectroscopy methods and fluorescence methods.

Optical sensing technology for detecting the presence of an analyte includes a number of different types of sensors.

One such type of optical sensor is known as distributed intrinsic chemical optical fiber sensors such as those sold under the trademark DICAST by Intelligent Optical Systems, Inc. of Torrance Calif. The distributed intrinsic optical fiber sensors use the cladding of an optical fiber to contain a sensing chemical, an indicator chemical. In this type of sensor the optical fiber acts as both the sensing means and the transmission means for the signal and allows sensing over a considerable length of such distributed intrinsic optical fiber. Changes in the cladding caused by reaction of the sensing chemical change optical parameters of the light passing through the core of the fiber. Typically the change in the sensing chemical is a change in color and the change in the light is a change in absorption, which changes the intensity of the light that leaves the sensor. See for example U.S. Pat. Nos. 4,834,496 and 7,260,283 and 7,650,051 and 7,551,810 and 7,583,865 which are assigned to the assignee of this patent and the contents of which are incorporated herein by reference.

Another type of sensor called an "optrode" is a small body of material such as glass in which sensing chemistry is imbedded or on which sensing chemistry is coated. Optrodes are known as "point" sensors because they are small and can sense the presence of an analyte at only a particular point or a small area. An optrode sensing system may use optical fibers to carry a signal to and from the optrode. See for example U.S. Pat. Nos. 6,535,658 and 4,399,099 the contents of each of which are incorporated herein by reference.

More generally various types of waveguide configurations may be constructed with a sensing coating in which a parameter of the light passing through the waveguide will vary when the sensing coating is affected by an analyte that reacts with a sensing chemistry in the coating.

BRIEF DESCRIPTION OF THE DRAWINGS

FIG. 11 is a chart of experimental results of light absorption in an optical fiber exposed to Soman GD.

DETAILED DESCRIPTION

Figure 1:
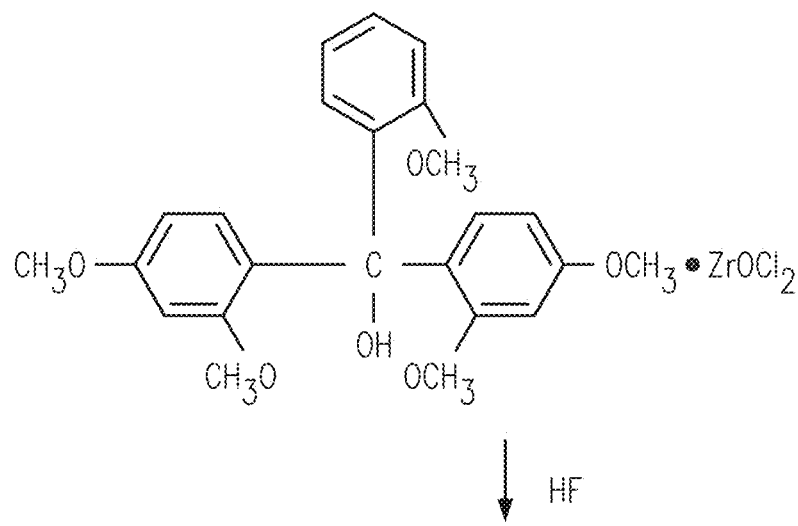
FIG. 1 is a diagram of an embodiment of the chemical processes of the invention.
Figure 1:
Figure 1:
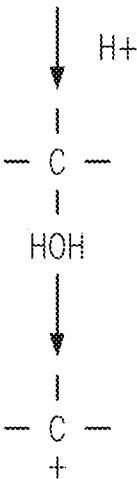

This Detailed Description incorporates by reference the content of U.S. Pat. Nos. 4,399,099; 4,834,496; 4,846,548; 5,138,153; 5,378,432; 6,535,658; 7,260,283; 7,650,051; 7,551,810; 7,583,865; 7,671,325 and 7,702,189.

The present invention embodies a sensing chemistry that is responsive to the presence of fluoride containing gaseous species and, in particular embodiments to the presence of Sarin (Sarin is also designated as GB) and Soman (Soman is also designated as GD) nerve gases. Actually, the sensing chemistry is responsive to HF as the decomposition product of fluoride gaseous species including Sarin and Soman gases and with that understanding for purposes of this discussion reference to the presence of fluoride gaseous species as well as to Sarin, and Soman means the presence of their decomposition by-product HF. As will be seen below, experimental confirmation will be obtained using diisopropyl fluorophosphate (DFP) which is well known as a simulant for Sarin and Soman.

Broadly speaking, the sensing or indicator chemistry is a pH dye component complexed with a heavy metal salt component which components function in the first condition to render the dye an in-active pH indicator but which is released upon exposure to HF allowing the dye to change color.

The more specific complex embodiment is selectively responsive to the HF decomposition by-product of nerve gas while not being responsive to other toxic gases, in particular HCN, $H_2S$, $Cl_2$ and HCl.

In other embodiments, sensing using the indicator chemistry can be embodied in a variety of optical sensor contexts including various forms of waveguides in which the dye is immobilized in combination with an optically conductive waveguide element. Thus color change of the dye is detected as a parametric change in light passing through the waveguide.

In some aspects the invention is embodied in the use of optrodes as waveguides.

In some aspects the invention is embodied in the use of distributed intrinsic chemical sensing optical fibers. The structure and functioning of this type of sensor is described in the reference patents noted above, the content of which are incorporated by reference herein. In further relationship to that aspect, one form of the chemical is particularly advantageous for distributed intrinsic chemical sensing sensors because the dye changes from a lighter color to a darker color. This is advantageous because by starting with a lighter color there is lesser absorbance along the length of the sensor, which allows for longer lengths and relief of the need for higher powered light through the sensor. The change in color, from lighter to darker can be sensed through parametric changes in the light, such as changes in intensity resulting from a change in adsorption, in particular resulting from a lesser to a greater absorbance caused by the color of the cladding from a lighter to a darker color.

In still further aspects the sensing is comprehended by a system in which a sensor is incorporated.

A further aspect the invention is embodied in chemistry for detecting the presence of a labile fluoride ion based on the discovery that by selecting a pH dye according to a specific set of characteristics and by complexing the dye with a heavy metal salt which has an affinity for fluoride, the set of possible dye reactions can be limited to a reaction with a molecule with a loosely bound fluorine. In such applications a pH of about 1.0-4.5 is applicable.

In yet further aspects methods are described for implementing the various aspects of the invention.

Further aspects of the invention are applicable to the detection of HF. For example, a fluoride-containing gas such as Sarin and Soman (insofar is mixed with its decomposition product HF) can be targeted specifically by selecting a pH dye with a pH in the range of about 1.2 to 2.3 and which has a hydroxyl group and has the ability to complex with a heavy metal salt comprising Zirchonyl Chloride, whereby a complex is produced specifically targeted for sensing a fluoride containing gas such as Sarin or Soman by changing color. A Copper metal salt may also be used however, optimum results were noticed with Zirconyl Chloride.

The invention may be applied to a variety of applications where detection of toxic gases and liquids/aerosols is a requirement. Major applications include protection of buildings and public venues (shopping and convention centers, sports arenas), mobile and transportation assets (aircraft, ships, rail systems), perimeter protection, large area verification of decontamination, leak detection, chemical concentration profiling, and air monitoring for mining safety. The area for which detection is sought is referred to herein as the surveillance area, or area under surveillance.

The invention is predicated on the observation that detection of a gas attack leaves little time for reaction to that attack. Therefore sensing priority is on being able to place sensors at a distance from areas and people to be protected and to provide time for reaction as well as to be able to have surveillance of a substantial area. Detection of low levels of Sarin and Soman gas is also an important goal.

According to an embodiment of the present invention, at the interface between a core and a cladding of a waveguide (such as a fiber optic cable), an indicator molecule is chemically responsive to a nerve gas—such as the Sarin and Soman decomposition product hydrogen fluoride—for causing a photodetector to detect a change in light guided through a fiber optical cable by a change in intensity, in particular from a higher to a lower intensity.

In one embodiment, the indicator molecule is pentamethoxy red, known under the acronym PMR (pH 1.2-2.3). In use the PMR reacts with or the Sarin or Soman decomposition product which is hydrogen fluoride. For purposes of development and testing the indicator chemistry is reacted with diisopropyl fluorophosphate (DFP) vapor, DPF is a recognized simulant for Sarin and Soman gas. The term pentamethoxy red and its acronym PMR are used here as an informal designation for the chemical 2, 2', 2", 4, 4'-pentamethoxytriphenylmethanol also known as Bis (2, 4-dimethoxyphenyl) (2-methoxyphenyl) methanol.

PMR has been determined to give the best response to DPF vapor compared to all previously investigated indicators. PMR can be complexed with different metal salts. $Cu^{+2}$ and $Zr^{+4}$ were successfully tested for complex formation with PMR. $Zr^{+4}$ in the form of Zirconyl Chloride ($ZrOCl_2$) showed a significant enhancement in the PMR response to DFP vapor. Cross-response tests were performed to answer the remaining cross-reactivity question against each of HCl, $H_2S$, HCN, and Chlorine gas. The results indicated no reaction of those other gases the PMR-$ZrOCl_2$ complex. The PMR-$ZrOCl_2$ complex upon exposure to HF causes the reactions seen in FIG. 1. In the reaction process, the $ZrOCl_2$ is cleaved from the PMR due to the greater affinity to complex with the flourine atom of the HF, which liberates the $H^+$ ion which then interacts with the hydroxyl group of the released PMR to produce a pH change and hence a color change in the dye.

The PMR-$ZrOCl_2$ complex is colorless in the absence of hydrogen fluoride. But when it is exposed to hydrogen fluoride gas the hydrogen fluoride reacts with the PMR-$ZrOCl_2$ producing a darker, purple colored, PMR. In the present context, that means, when the complex is exposed to Sarin or Soman, the chemical reactions take place and the PMR darkens.

The change in color to indicate the presence of Sarin or Soman may be used and observed in a number of ways, including human observation.

The change in color of the indicator molecule is implemented in the optical sensing means and methods. The color change from light to dark is particularly applicable in the case of distributed intrinsic optical fiber sensors because those sensors operate over a considerable distance and the availability of a sensing chemistry that allows the cladding to be light in color is beneficial to absorption over the length allowing an extended length to be operable. The change to a darker color increases absorption and gives a reduction in intensity of the observed light at the output end which reduction in intensity is used as the precursor to a warning.

As noted above, the indicator molecule is specific for the Sarin and Soman decomposition product, hydrogen fluoride, and does not react with HCN, $H_2S$, $Cl_2$ and HCl.

The optical fiber which is part of the invention is itself the sensing element and is constructed into a rugged cable, creating a field-installable chemical sensor with continuous and sensitive detection capability over its entire active length.

Figure 2:
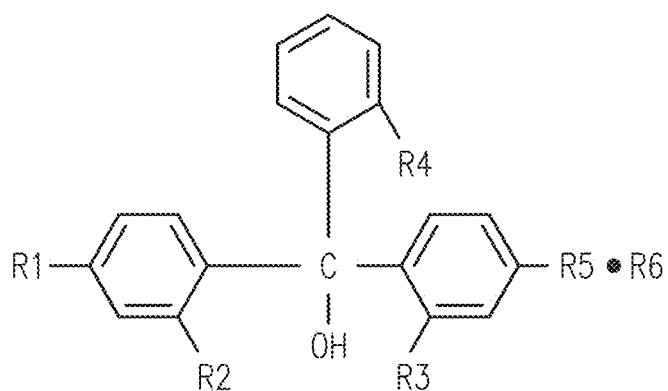
FIG. 2 is a diagram of a generic form of a chemical complex for sensing.

The chemical reaction process is illustrated in FIG. 2 depicting the chemical structure of the indicator molecule PMR [2,2',2",4,4'-pentamethoxytriphenylmethanol—also known as—bis(2,4-dimethoxyphenyl)(2-methoxyphenyl) methanol] complexed with $ZrOCl_2$. The PMR-$ZrOCl_2$ complex is relatively light in color. Exposure to HF cleaves the complex and releases the PMR to act as a pH indicator dye. In this case the zirconyl chloride will react with the labile fluorine atom of the HF freeing the PMR to act as a pH indicator; the liberated $H^+$ ion will react with the PMR, binding to give off $H_2O$ leaving a carbonium ion. This modified PMR will now have a darker color such as purple.

The indicator molecule is inactive to other toxic gases, in particular HCN, $H_2S$, $Cl_2$ and HCl.

It is considered that any alkoxy group and more specifically ethoxy may be substituted for the methoxy group of PMR. Thus, the indicator molecule can be pentamethoxy red, pentaethoxy red, or generally pentalkoxy substituted triphenyl carbinol. FIG. 2 illustrates the generic structure for the complex in which it is considered that substitutions R1 through R4 can each be an alkoxy group more specifically the methoxy group as shown in FIG. 1 for PMR and an ethoxy group, and R6 can be a heavy metal salt and more specifically copper sulfate and zirconyl chloride. The following experiments confirm aspects of the invention as indicated.

Experiment 1

A pentamethoxy red complexed with zirconyl chloride in methanol solution was made with 10 grams/liter. A sufficient amount of the methanol/indicator molecule solution was introduced into a silicone acrylate formulation (DESO-LITE® 114E a proprietary product of DeSoto, Incorporated) to produce a 0.2 percent by weight dye concentration. The composition containing the dye was placed in an applicator. The applicator was put on a fiber draw tower 3 meters from the fiber drawing furnace.

An undoped silica quartz rod (SUPRASIL® 2, a product of Heraeus-Amersil) was drawn at 0.9 m/sec into a fiber core having a diameter of approximately 125 microns. The fiber core was routed through the indicator-molecule-containing composition in the applicator and through a hole at the bottom of the applicator, which produced a coating having an outside diameter of 230 microns. The coating was cured by passing the coated fiber near a UV lamp made by Fusion Systems. At the draw speed employed this lamp produced a UV dose of approximately 1 Joule per square centimeter in the 300 to 400 nm spectral range. The fiber was then wound on a drum. The process was continued until several hundred meters had been drawn.

To produce a control, the same procedure was followed but the indicator molecule was omitted from the silicone acrylate resin. The spectral loss for both the control sample and the indicator-molecule-containing sample were measured by comparing the light intensity transmitted through a long length of fiber to that transmitted through a short length. For the control fiber, the long length was 50 meters and the short length was 1 meter. For the indicator-molecule-containing fiber the long length was 50 meters and the short length was 1 meter. The spectral loss of the indicator-molecule-containing fiber peaked at 650 nm and was higher relative to the control by 40 dB per kilometer.

Figure 3:
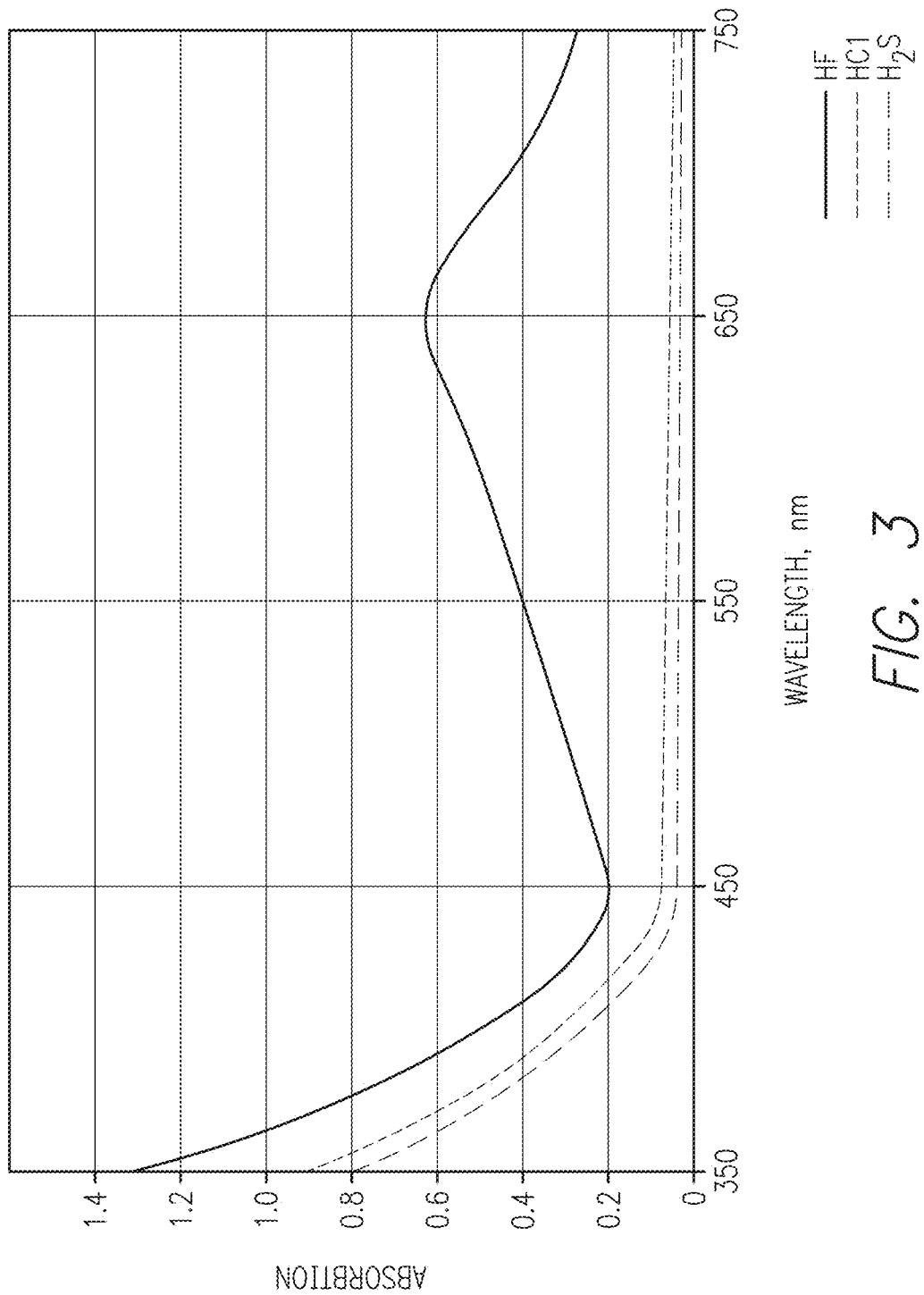
FIG. 3 is a chart of absorption vs. wavelength comparing the chemistry of FIG. 1 for its absorption sensitivity for HF, $H_2S$ and HCl.
Figure 12:
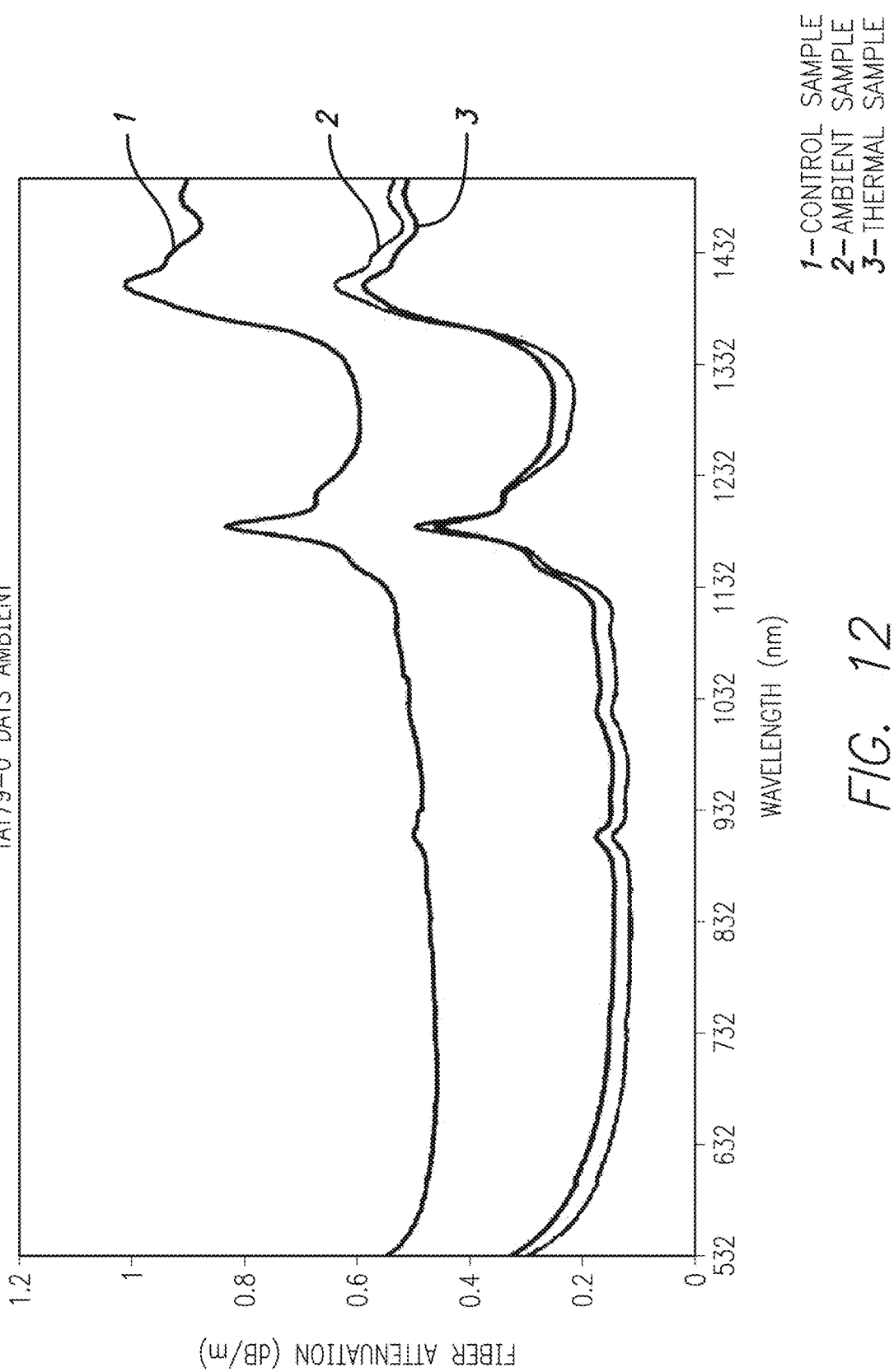
FIG. 12 is a chart showing fiber attenuation variation over a frequency range.
Figure 13:
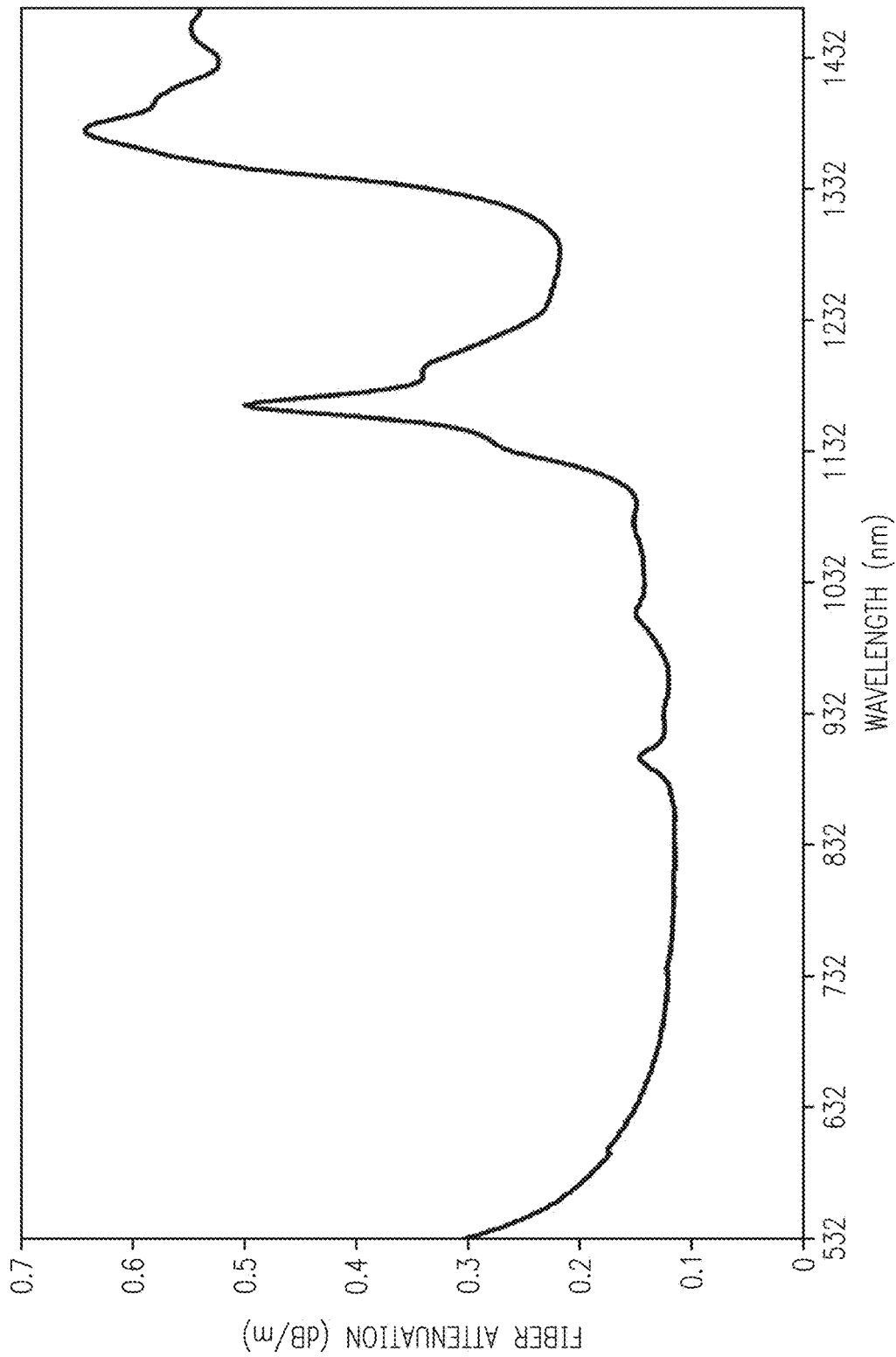
FIG. 13 is a chart of the average of the traces in FIG. 12.

A 10 m length of indicator-molecule-containing fiber was placed in a one gallon closed container with ends exiting the container and extending to the spectral loss test set. The loss spectrum of the fiber was measured and was as shown in FIGS. 12 and 13. Subsequently, light at a wavelength of 650 nm was launched into one end of the fiber and the light output at the other end was continuously monitored. The intensity of light exiting the fiber at a wavelength of 650 nm was measured as a function of time starting at the introduction of ammonia and continuing for approximately 500 seconds. Measurable changes in the observed intensity commenced approximately 7 seconds after introduction of ammonia. When the observed optical change reached equilibrium the total loss change was approximately 360 dB per kilometer. Approximately 90 percent of the change occurred within the first 40 seconds. The presence of hydrogen fluoride was readily detectable while the presence of hydrogen sulfide and hydrogen chloride was generally too low for practical detection. These results are shown in FIG. 3.

Experiment II

Figure 4:
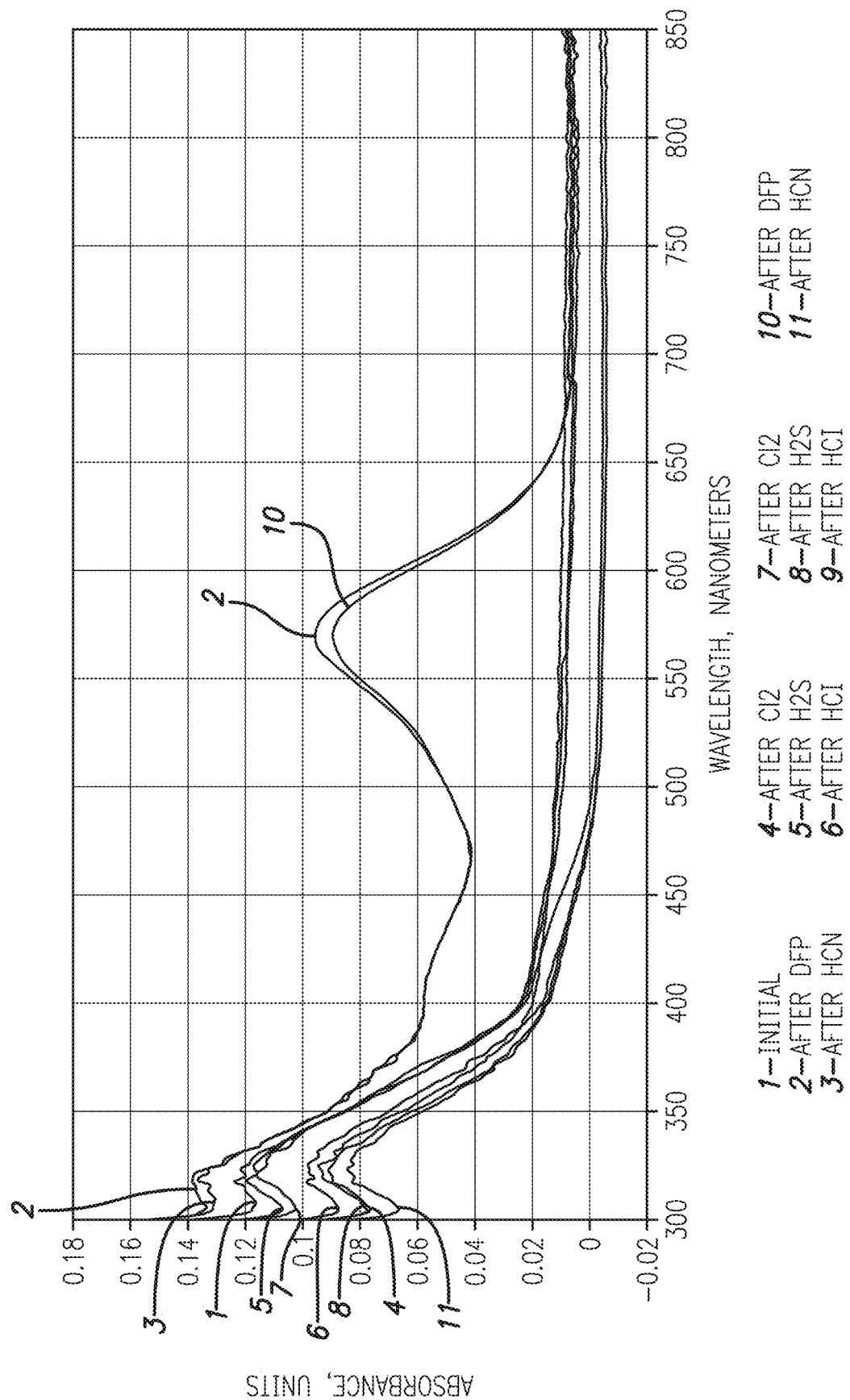
FIG. 4 is a chart of experimental results of spectral changes in the PMR-$ZrOCl_2$ complex against exposure to DFP, $Cl_2$, HCL, HCN and $H_2S$.

Following the procedures of EXPERIMENT I, the results of testing for cross-response of the PMR-zirconyl chloride complex to DFP, HCN, $H_2S$, $Cl_2$ and HCL are shown in FIG. 4. In this graph the absorption of the PMR-zirconyl chloride complex from exposure to DFP is much greater relative to the other analytes in which absorption is generally nil.

Experiment III

Figure 5:
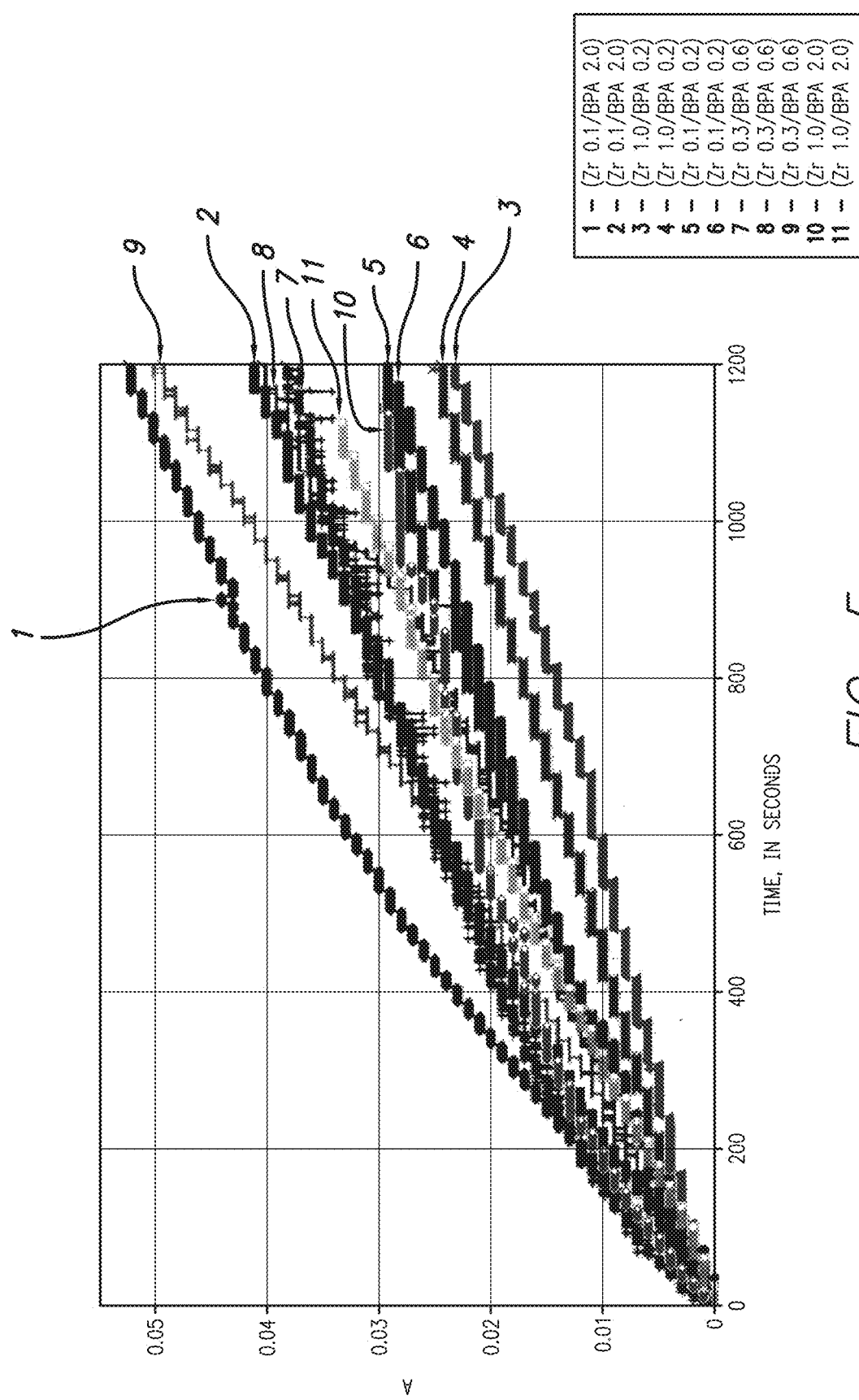
FIG. 5 is a chart of experimental results of the response to DFP gas of various concentration levels of the PMR-$ZrOCl_2$ complex in a selected polymer along with varying amounts of a hydrolyzing agent (BPA).

In an effort to optimize the response to DFP gas (increased response magnitude, reduced response time) various concentration levels were investigated for PMR and $ZrOCl_2$ in a selected polymer that is suitable as a fiber cladding. The polymer is a UV curable polyurethane acrylate. Additionally, a hydrolyzing agent (Bisphenol A, BPA) was used to enhance the DFP hydrolysis rate and hence reduce the response time. The ZrOCl$_2$ was used at the range of 0.1, 0.3 and 1.0% w/w while the BPA was used at 0.2, 0.6 and 2.0% w/w. At each concentration level, films were spun coated and UV-cured resulting in 18-22 um thick films. These films were subjected to testing with 100 ppm DFP. The results are shown in FIG. 5.

Example IV

Figure 6:
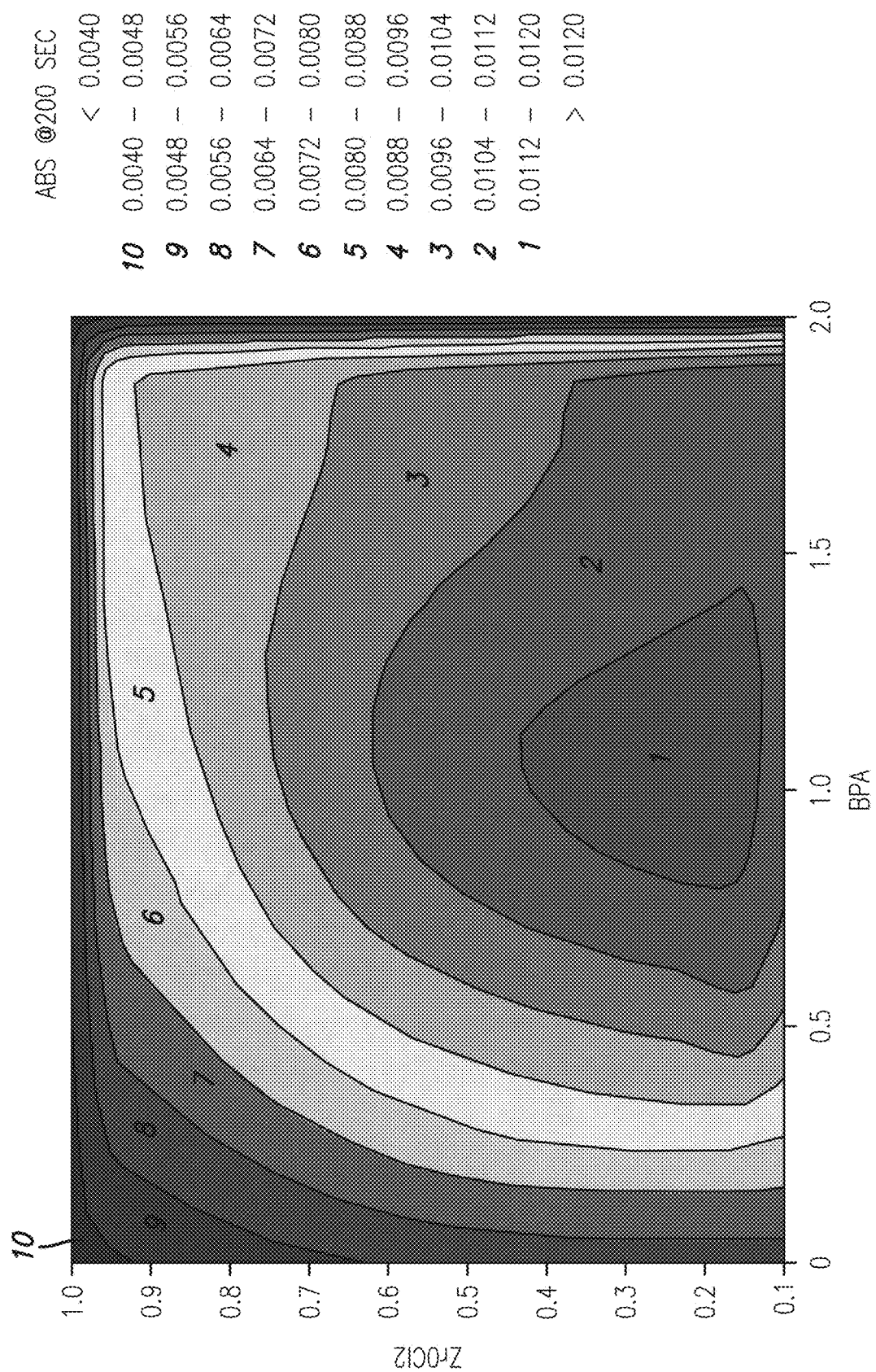
FIG. 6 is a contour plot of the experimental results of FIG. 5 as a function of response magnitude.
Figure 7:
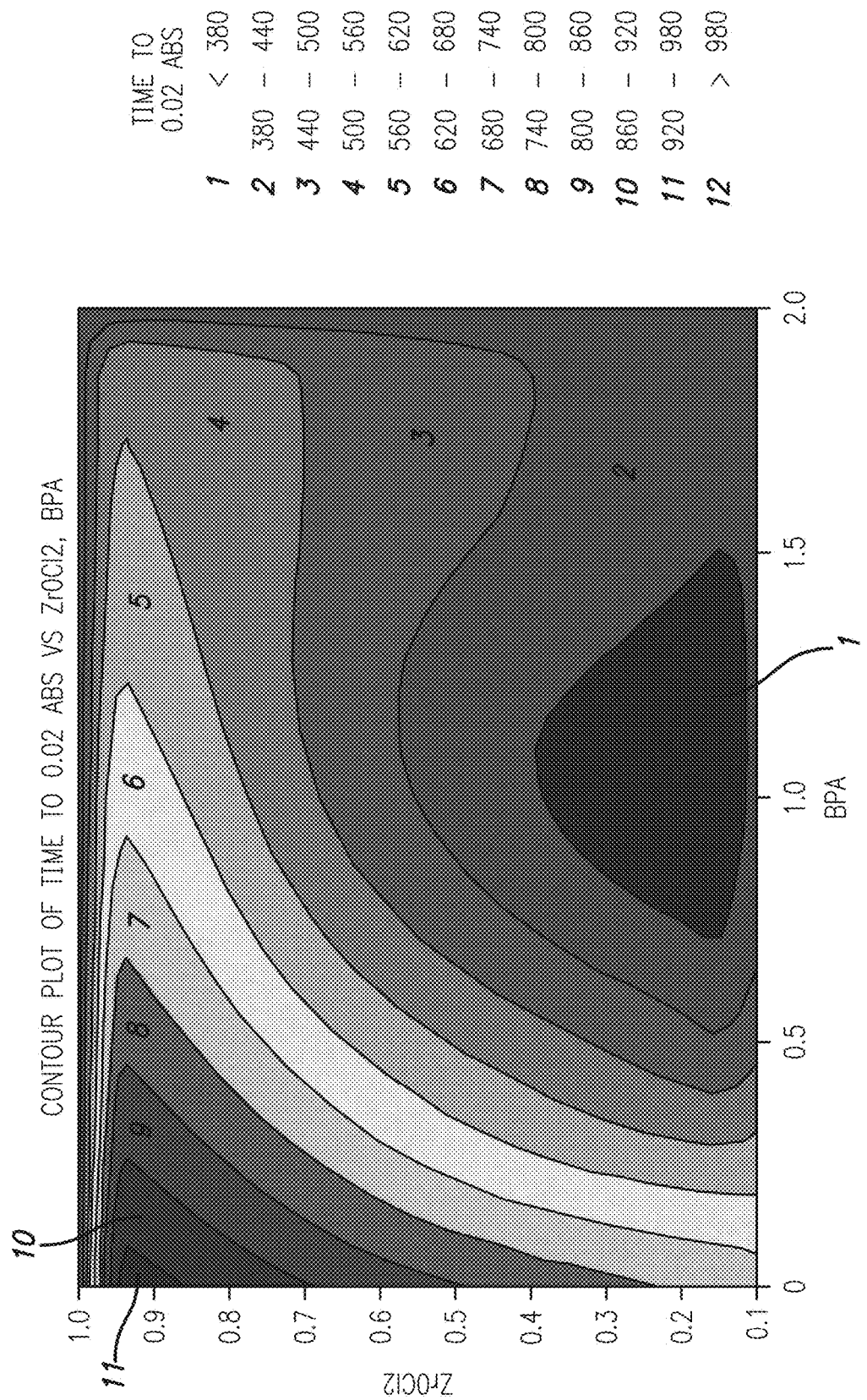
FIG. 7 is a contour plot of the experimental results of FIG. 5 as a function of response time.

The data from Example III were extracted from the above experiments and plotted as in FIG. 6 as a 3D contour plot as a function of response magnitude while FIG. 7 presents the data as a function of response time. Both plots favored a beneficial formula for both high signal and fast response time to be in the range of about 0.7 to about 1.5% BPA and about 0.15 to about 0.4% ZrOCl$_2$ (w/w) and the optimum formula for highest signal and fast response time to be about 1.0 to about 1.5% BPA and about 0.2 to about 0.4% ZrOCl$_2$. (w/w).

Experiment V

Figure 8:
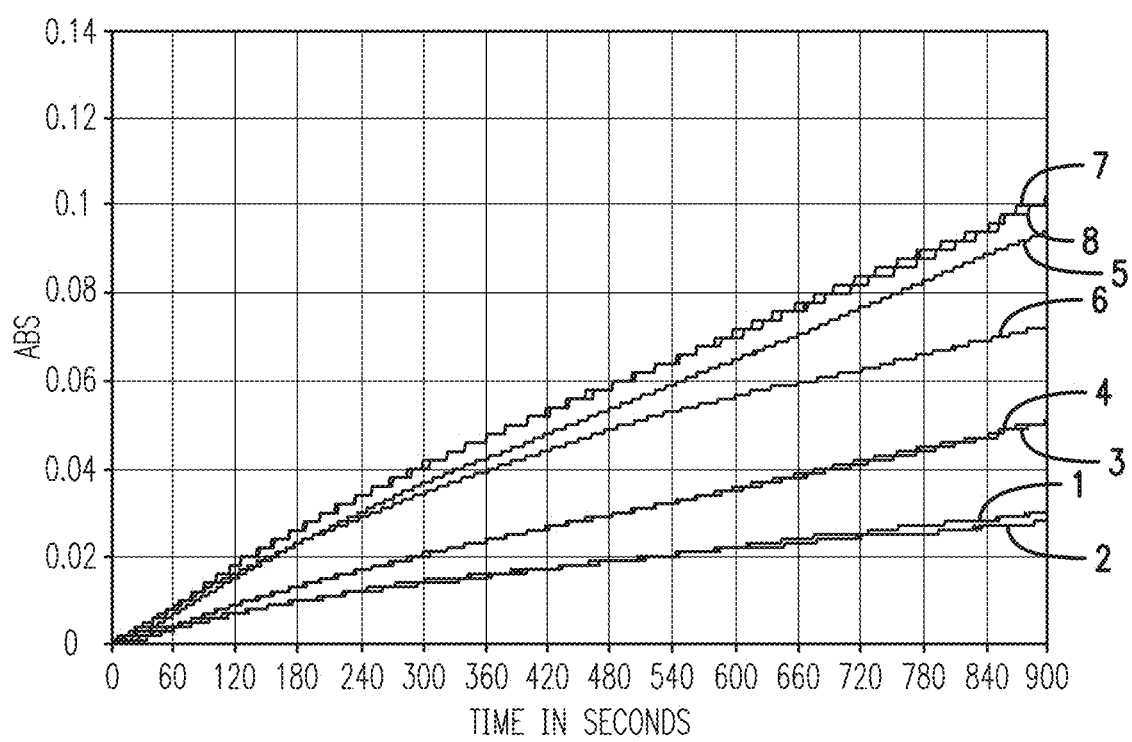
FIG. 8 is a chart of an optimum formulation tested against various concentrations of DFP vapor to determine dynamic range and sensitivity; determining time-based acquisition response.

The optimum formulation was tested against various concentrations of DFP vapor to determine the dynamic range and the sensitivity. FIG. 8 illustrates the time based acquisition response of the optimum formulation against various DFP vapor concentrations.

Experiment VI

Figure 9:
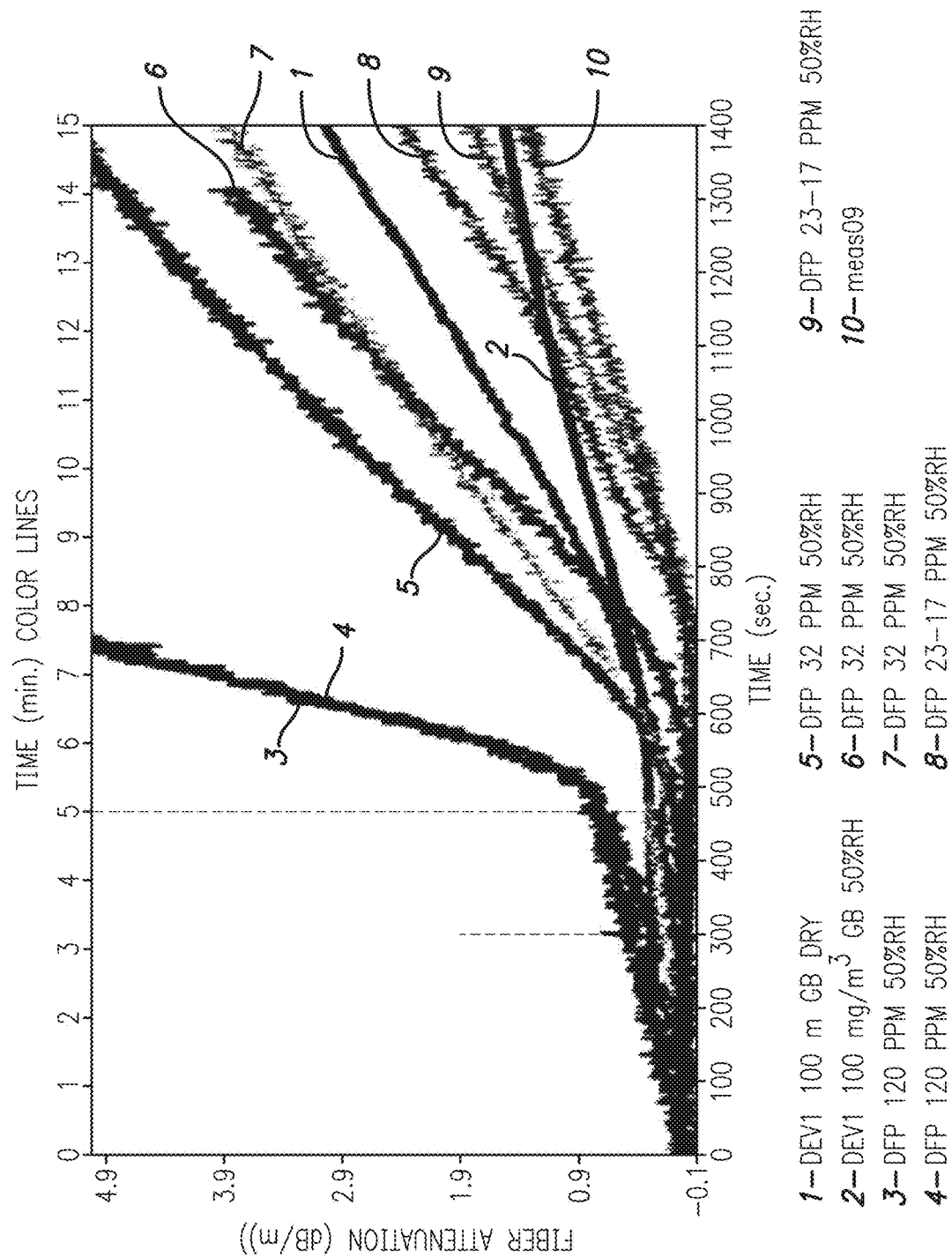
FIG. 9 is a chart of the response of an optical fiber using the optimum formulation tested against various levels of DFP; indicating response as a function of time; also presenting the fiber response to live agent (Sarin, GB) at 100 $mg/m^3$.

Distributed intrinsic optical fiber was drawn using the above formulation and tested against various levels of DFP. FIG. 9 illustrates the response of the fiber as a function of time.

Figure 10:
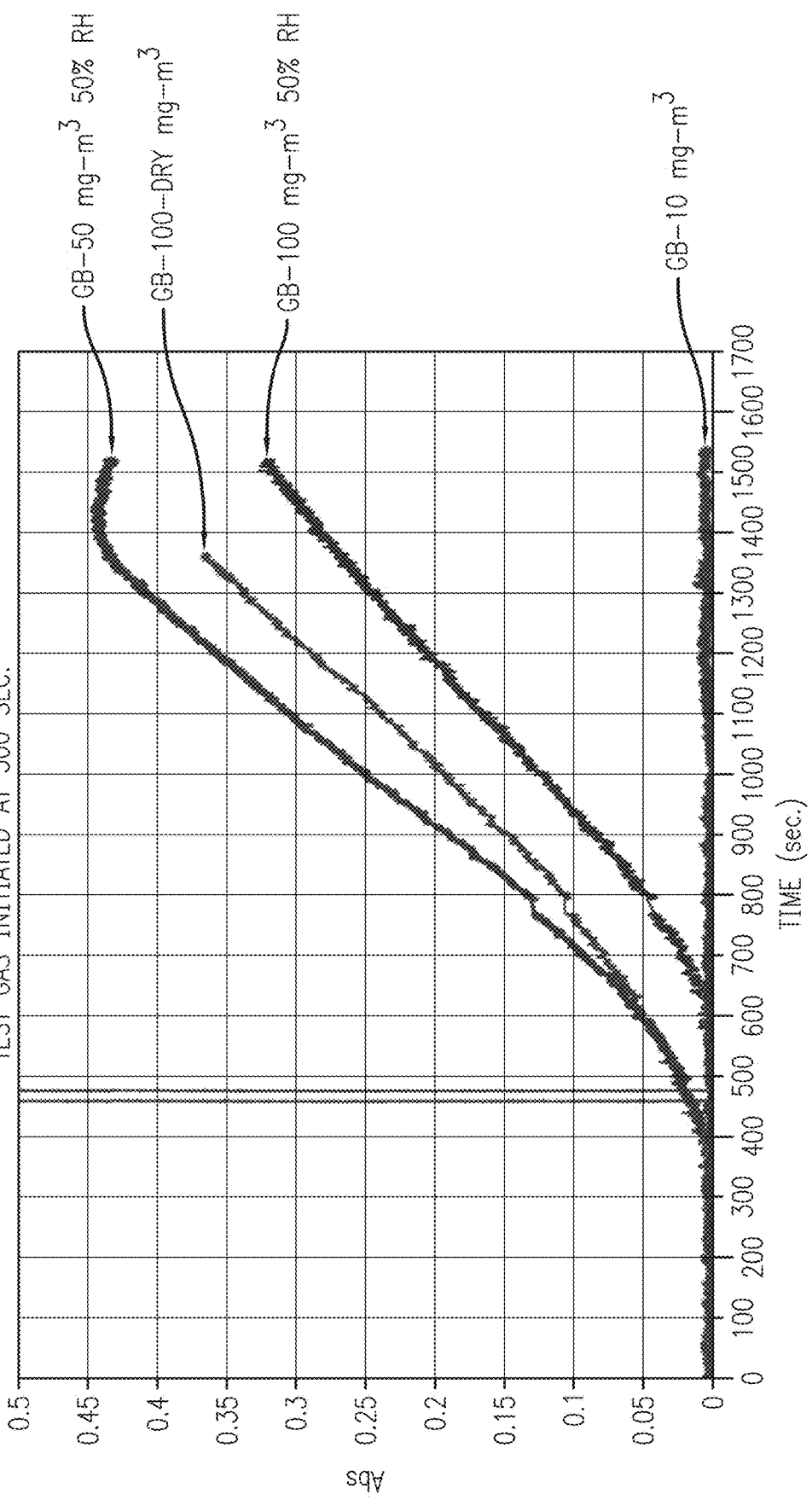
FIG. 10 presents the effect of different GB levels on the response of an optical fiber as a function of time.

FIG. 9 also presents the fiber response to live agent (Sarin GB) at 100 mg/m$^3$, while FIG. 10 presents the effect of different GB levels on the response of the fiber as a function of time.

FIG. 10 shows the results of fiber testing against 100 and 10 mg/m$^3$ of Soman GD.

It is considered that the indicator molecule, that is the complex can be more generally defined in which the dye is a triphenyl carbinol, which may be substituted or unsubstituted in which other alkoxy groups can be substituted for the methoxy group of pentamethoxy red (PMR). More particularly, it is considered that a homologue substitution for the methoxy group is a functionally equivalent embodiment and in particular, ethoxy.

The particular application of the chemical aspect of the invention in combination distributed intrinsic optical fiber sensing will now be described.

While detection of gases by distributed intrinsic optical fiber sensing technology is understood the following is set out for the present invention.

The invention in the form operative with an evanescent field, operates on the principal of ATR (Attenuated Total Reflection); the light guiding properties of optical fiber are affected when the target chemical agent reacts with an embedded chemical indicator in the cladding or adjacent coating to the core such that the indicator chemistry is within the evanescent field adjacent the core/cladding or coating interface. For simplicity, the material covering the core will be referred to as the cladding whether it is a single body or multiple bodies of material. The change in the transmission properties of the light received at a distal end of the fiber is detected using signal processing algorithms designed to maximize sensitivity and minimize false alarms.

Upon exposure, the chemical agent to be detected diffuses into the cladding and reacts with the indicator molecule, causing the cladding to change color from a lighter to a darker color. The reaction consumes only a portion of the dye in most cases, allowing for the detection of multiple chemical exposures. The evanescent field of light reflected at the core/cladding interface interacts with the cladding and the color change results in attenuation of the light by the fiber through the well-known "cladding loss" phenomenon. That change is detected as reduction in intensity of received signal from the optical fiber. It is also known that the change can be from a darker to a lighter color, in which case the output intensity increases, but the lighter-to-darker color change is needed in order to enable the use of longer lengths of fiber.

In the absence of a chemical agent, when a ray of guided light in the core is totally reflected at the core-cladding interface, a non-propagating electromagnetic field, an evanescent field, briefly exists in the region of the cladding close to the core. When a chemical agent triggers a color change in indicator molecules embedded in the fiber cladding, the cladding absorbs light from the evanescent field, resulting in a change in fiber attenuation at wavelengths relating to the color change. This results in loss of light intensity at the output end of the fiber.

The fiber attenuation in dB is represented by $$\text{Attenuation} = -10 \cdot \log \frac{P(z)}{P_0},$$

where the logarithm of the ratio of the final light intensity is ($P_z$) and the initial light intensity is ($P_0$). The relationship of fiber attenuation with the change in color is assessed to be linear and is generalized here using Beer's Law:

$$-\log \frac{P(z)}{P_0} = abc = \text{Absorbance},$$

where a is the absorption coefficient of the indicator, b is the length of exposed fiber (pathlength), and c is the concentration of the 'exposed' indicator. The sensitivity is then a function of the length (amount) of fiber exposed, with high sensitivity achieved due to the extended length of the sensor (very high sampling).

The fact that the fiber attenuation change is due to a (wavelength-specific) change in the cladding optical absorbance means that wavelengths far from the absorbance of the indicator molecule are unaffected by the presence of the chemical agent. This allows the invention to be self-calibrating and self-referenced. By launching and detecting light at two wavelengths, one at the indicator dye's absorbance maximum and one outside of the absorbance band, the optoelectronic system can detect the difference between signal changes caused by such spurious effects as fiber bending or temperature-induced refractive index changes (which affect both wavelengths) and permeation of the target chemical (which only affects one wavelength).

Figure 14:
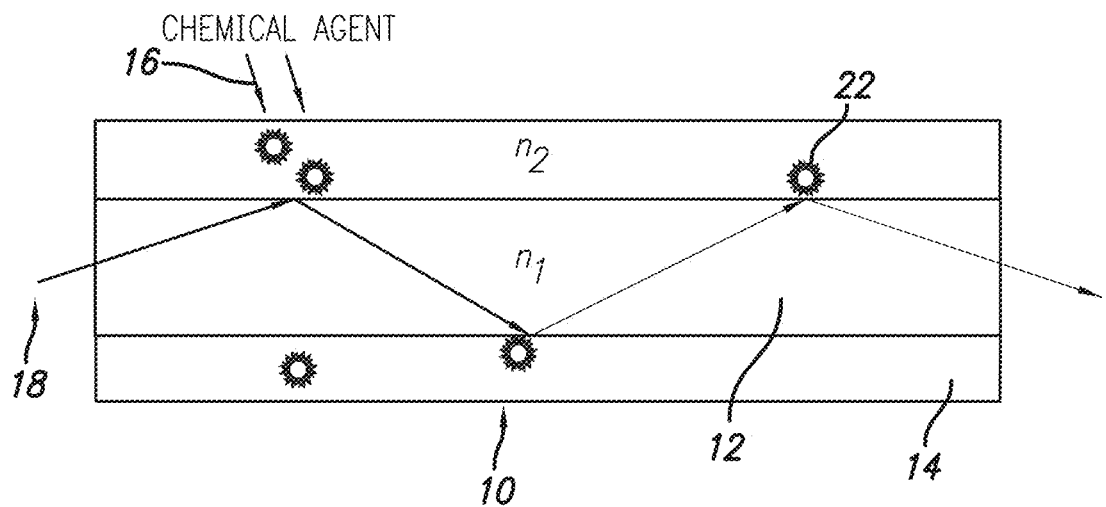
FIG. 14 is a schematic diagram of an optical fiber of the invention.

FIG. 14 is a side diagrammatic view of the fiber optical cable of the present invention (not to scale). A fiber optic cable 10 includes a core 12 surrounded by a cladding 14 and in most cases covered by a gas permeable jacket (not shown). Also, there may be a coating over the core, but sufficiently thin that the evanescent field still projects into the cladding (or, alternatively the coating may include the indicator chemical). In this description any and all coatings on the fiber core are referred to as cladding. Fiber optic cable 10 is permeable to an ambient chemical agent 16 into the cladding which may be a nerve gas decomposition product. Specifically, the chemical agent 16 may be hydrogen fluoride, which is a decomposition by-product of Sarin and Soman gases.

In FIG. 14, in the absence of a nerve gas or its decomposition by-product, light 18 is guided through the fiber optic cable 10 with minimal or at least a baseline attenuation. The lower the attenuation, the longer may the fiber be. Indicator molecules 22 disposed within the cladding 14—when exposed to the chemical agent 16—reacts with the chemical agent 16 causing the indicator molecule 22 to change from a first state (preferably a lighter color) to a second state (a darker color) and this change results in a parametric change in the light transmitted. In this exemplary case the parametric change to be measured is the increase in attenuation caused by darkening of the cladding resulting in decreased intensity of light at the output end of the fiber. This result is sensed by a photodetector for providing a signal to an alarm system (see FIG. 16).

Figure 15:
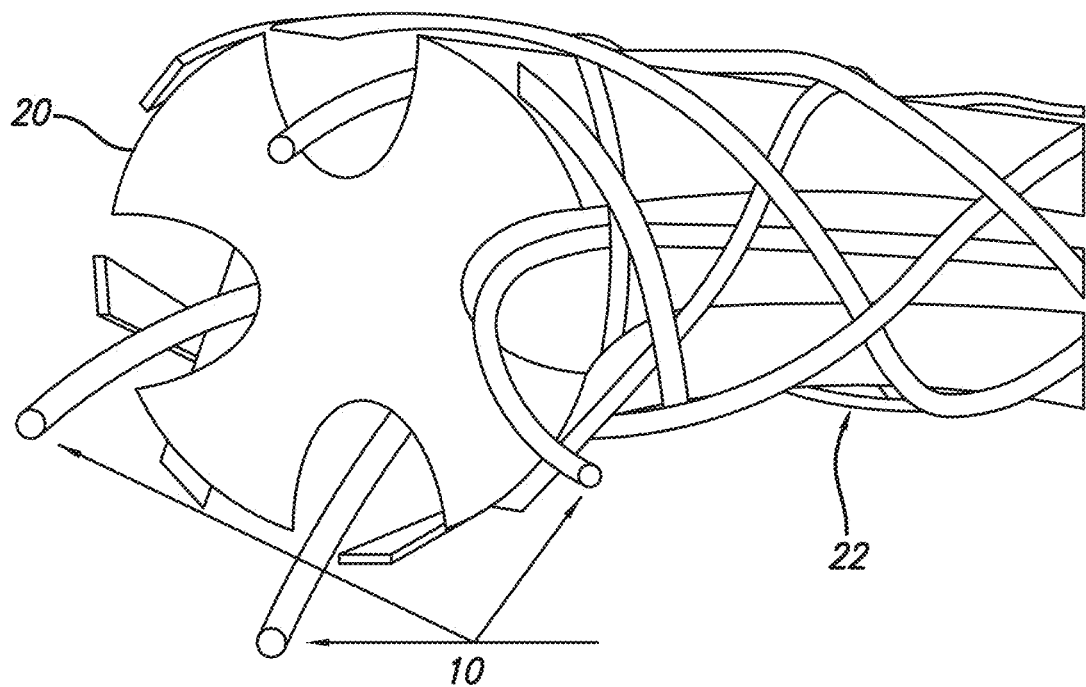
FIG. 15 is a schematic diagram of a multiple fiber cable as an embodiment of the invention.

FIG. 15 shows an end-on perspective view of an embodiment of the invention in which a plurality of optical fibers is used such as a group of fiber optic cables 10. Four fiber optic cables 10 are shown extending in slots in a central plastic support cable 20. The fiber optic cables 10 shown may each be capable of detecting the same event, (presence of Sarin and Soman) or different events (Sarin and Soman as well as some other chemical attack) and may include a non-reactive reference cable for a reference signal. An exemplary gas permeable jacket 22 is shown as a weave of fibers.

Figure 16:
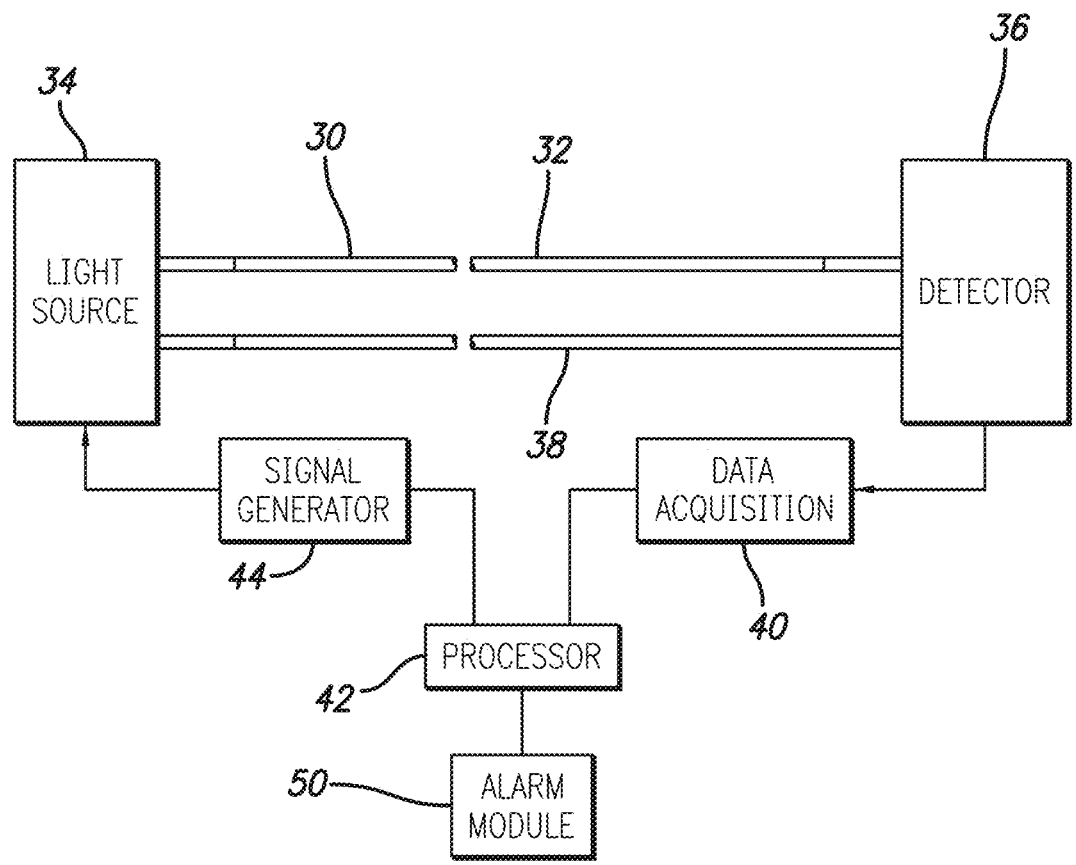
FIG. 16 is a schematic diagram of a system as an embodiment of the invention.

FIG. 16 is a schematic diagram of an illustrative embodiment of a system of the invention. A fiber portion 30 has a sensitized length 32 connected between a light source 34 and detector 36. Also, a reference cable 38 is connected between the light source and the detector. The received light is sent to the Data Acquisition module 40 at which it is converted to an electrical signal and then to the Processor 42. The Processor 42 has directed the Signal Generator 44 to output the designated light signals, for the detector fiber 30 and the reference fiber 38, which information is also directed to the Processor 42. The Processor 42 will operate to determine the comparative attenuation of the reference and the detector fiber to determine if the detector fiber has been so attenuated as to indicate a sensing event. If a sensing event is determined a warning signal is sent to the alarm module 50. The signal to the alarm module can be based on selected determinations made by the Processor about the nature of parametric changes to the light caused by the sensing event. Then, the alarm module can respond at selected determinations, the alarm module can be any type of output device that can provide a simple alarm, or for example a monitor that can provide more detailed output information, and of course there can be a communication set-up to send information to remote receivers. Of course, the system can be operated without a reference signal in which case only the change in the active fiber is measured.

Figure 17A:
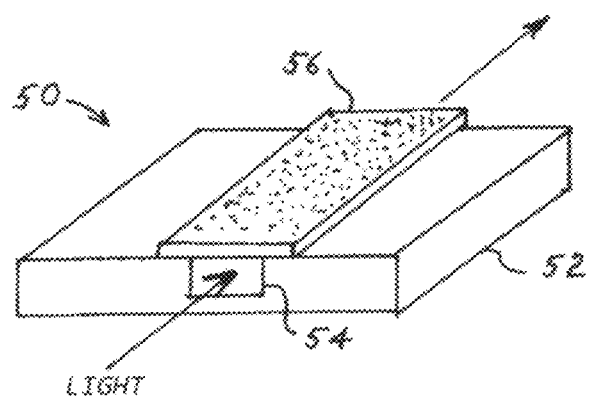
FIG. 17A is a schematic diagram of a waveguide form of the invention.
Figure 17B:
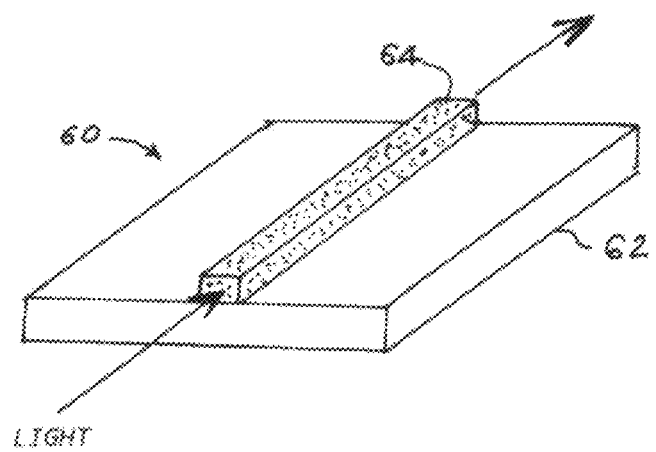
FIG. 17B is a schematic diagram of a different waveguide form of the invention.

FIG. 17A schematically shows a generic waveguide sensor 50 which has a substrate 52 and a waveguide portion 54 in the substrate with its upper surface exposed and in which the sensing chemistry indicated as dots, is in a film 56 in place adjacent the waveguide portion 54, similarly to the fiber optic structure described above, to cause a response in the light passing through the waveguide from a color change in the film 56. This can be considered an evanescent wave type sensor. FIG. 17B shows another type of waveguide sensor 60 which has a substrate 62 and a waveguide portion 64 mounted on the substrate 62. In this case the sensing chemistry, indicated as dots, is incorporated into the body of the waveguide portion. In this case the color change is in the waveguide portion 64 itself causing a parametric change in the light passing through it.

Although in the foregoing descriptions the specific parameter whose variation is detected is change in intensity, other parameters can also be used with the indicator chemistry of the invention, such as change in refractive index of the indicator coating or cladding or a wavelength shift or other parameters as known.

While various embodiments have been chosen to demonstrate the invention, it will be understood by those skilled in the art that various modifications and additions can be made without departing from the scope of the invention as defined in the appended claims.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . "

I claim:

1. A chemical sensor comprising:
   a polymer-based substrate permeable to a predefined target chemical substance, the polymer-based substrate comprising:
      an embedded chemical indicator, wherein the optical properties of the polymer-based substrate change when exposed to the predefined target chemical substance causing a parametric change of light passing through the polymer-based substrate, and
      wherein the embedded chemical indicator comprises an indicator dye complexed with a heavy metal salt, whereby the indicator dye is rendered inactive and which heavy metal salt is preferentially functional to complex with a fluoride ion by cleaving from the indicator dye, and wherein a hydrolyzing agent is embedded in the polymer-based substrate.

2. The chemical sensor of claim 1 for detection of Sarin and Soman nerve gases by detection of their decomposition by-product hydrogen fluoride (HF) and the indicator dye having an available hydroxyl group;
whereby upon exposure of the complex to the HF the metal salt will cleave from complex with the dye and complex with the fluoride ion and the resulting proton H+ will react with the hydroxyl group of the dye rendering the dye available to change color.

3. The chemical sensor of claim 1 wherein the hydrolyzing agent is bisphenol a (BPA).

4. The chemical sensor of claim 1 wherein indicator dye is substituted or unsubstituted triphenyl carbinol.

5. The chemical sensor of claim 1 wherein the heavy metal salt is zirconyl chloride or copper sulfate.

6. The chemical sensor of claim 1 wherein the indicator dye is a substituted triphenyl carbinol of the formula

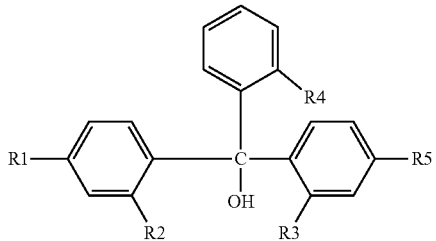

wherein RI, R2, R3, R4 and R5 each, independently of the others is an alkoxy group.

7. The chemical sensor of claim 6 wherein RI, R2, R3, R4 and R5 are each a methoxy group or ethoxy group.

8. The chemical sensor of claim 7 wherein the heavy metal salt is zirconyl chloride.

9. The chemical sensor of claim 1 wherein the indicator dye is 2,2',2'',4,4'-pentamethoxytriphenylmethanol also known as Bis(2,4-dimethoxyphenyl)(2-methoxyphenyl) methanol also known as pentamethoxy red.

10. The chemical sensor of claim 1 wherein the heavy metal salt is zirconyl chloride.

11. A method for detecting a target chemical of which hydrolyzed fluoride ion is a decomposition by-product comprising:

providing a polymer-based substrate permeable to a predefined target chemical substance, the polymer-based substrate comprising an indicator dye having an available hydroxyl group rendered inactive by being complexed with a heavy metal salt (the complex) which is functional to be cleaved by a fluoride from hydrogen fluoride preferentially to complex with the fluoride ion whereby the dye is rendered active for dye reaction, and
wherein a hydrolyzing agent is embedded in the polymer-based substrate;
exposing the complex to an environment that is under surveillance for the target chemical of which hydrogen fluoride is a decomposition by-product;
detecting changes in the dye coloration indicative of the presence of hydrogen fluoride.

12. The method of claim 11 wherein the indicator dye is a substituted triphenyl carbinol of the formula

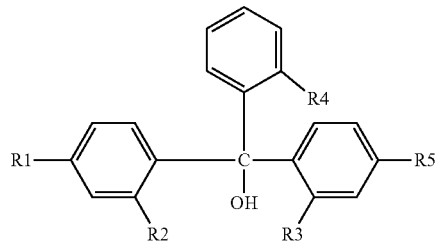

where in R1, R2, R3, R4 and R5 each, independently of the others is an alkoxy group.

13. The method of claim 11 where in the heavy metal salt is zirconyl chloride.

14. The method of claim 12 where in R1, R2, R3, R4 and R5 are an ethoxy or methoxy group.

15. The method of claim 11 wherein the target chemical is Sarin and Soman and the hydrolyzed fluoride ion is HF a decomposition by-product of Sarin or Soman.

16. The method of claim 11 wherein the indicator dye is 2,2',2'',4,4'-pentamethoxytriphenylmethanol also known as Bis(2,4-dimethoxyphenyl)2-methoxyphenyl)methanol.

17. The method of claim 11 wherein the indicator dye has a carbinal constituent and is complexed with a heavy metal salt.

18. The method of claim 11 wherein the complex is embedded in a polymer-based substrate.

* * * * *